United States Patent
Wang et al.

(10) Patent No.: US 9,797,776 B2
(45) Date of Patent: *Oct. 24, 2017

(54) LASER INDUCED BREAKDOWN SPECTROSCOPY (LIBS) APPARATUS BASED ON HIGH REPETITION RATE PULSED LASER

(71) Applicants: Sean Xiaolu Wang, Wilmington, DE (US); Qun Li, Newark, DE (US)

(72) Inventors: Sean Xiaolu Wang, Wilmington, DE (US); Qun Li, Newark, DE (US)

(73) Assignee: BWT Property, Inc., Newark, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/166,374

(22) Filed: May 27, 2016

(65) Prior Publication Data

US 2017/0067782 A1  Mar. 9, 2017

Related U.S. Application Data

(63) Continuation-in-part of application No. 14/845,980, filed on Sep. 4, 2015.

(51) Int. Cl.
*G01J 3/30* (2006.01)
*G01J 3/443* (2006.01)
(Continued)

(52) U.S. Cl.
CPC ........... *G01J 3/443* (2013.01); *G01J 3/0208* (2013.01); *G01J 3/06* (2013.01); *G01J 3/10* (2013.01); *G01J 3/28* (2013.01)

(58) Field of Classification Search
CPC ...... G01J 3/443; G01J 3/06; G01J 3/02; G01J 3/10; G01J 3/0208; G01J 3/28; G01J 3/44; G01J 3/30; G01N 21/63; G01N 21/718

See application file for complete search history.

(56) References Cited

U.S. PATENT DOCUMENTS

| 7,394,537 B1 | 7/2008 | Lindfors et al. |
| 7,999,928 B2 | 8/2011 | Beckstead et al. |
| (Continued) | | |

FOREIGN PATENT DOCUMENTS

CN  102735658 A  * 10/2012  ............. G01N 21/63

*Primary Examiner* — Jamil Ahmed

(57) ABSTRACT

This invention discloses a laser induced breakdown spectroscopy (LIBS) apparatus based on a high repetition rate pulsed laser. The laser produces a train of laser pulses at a high repetition rate in the kHz or even higher range. When the laser beam hits the sample, it generates several thousands of micro-plasma emissions per second. Synchronized miniature CCD array optical spectrometer modules collect the LIBS signal from these micro-plasma emissions. By adjusting the integration time of the spectrometer to cover a plurality of periods of the laser pulse train, the spectrometer integrates the LIBS signal produced by this plurality of laser pulses. Hence the intensity of the obtained LIBS spectrum can be greatly improved to increase the signal-to-noise ratio (SNR) and lower the limit of detection (LOD). In addition, the influence of pulse to pulse variation of the laser is minimized since the obtained LIBS spectrum is the spectrum of a plurality of micro-plasma emissions produced by a plurality of laser pulses. The high repetition rate laser also makes it possible to measure the LIBS signal at a short and a long integration time and mathematically combining the two spectra to obtain a LIBS spectrum with enhanced dynamic range.

16 Claims, 4 Drawing Sheets

(51) Int. Cl.
  *G01J 3/10*  (2006.01)
  *G01J 3/06*  (2006.01)
  *G01J 3/02*  (2006.01)
  *G01J 3/28*  (2006.01)

(56) References Cited

U.S. PATENT DOCUMENTS

2004/0051867 A1* 3/2004 Brestel .................. G01J 3/2889
  356/318
2008/0151241 A1* 6/2008 Lindfors .............. G01N 21/718
  356/318
2012/0033212 A1 2/2012 Barefield, II

* cited by examiner

LASER INDUCED BREAKDOWN SPECTROSCOPY (LIBS) APPARATUS BASED ON HIGH REPETITION RATE PULSED LASER

REFERENCE TO RELATED APPLICATION

This application is a continuation-in-part of U.S. application Ser. No. 14/845,980, entitled "LASER INDUCED BREAKDOWN SPECTROSCOPY (LIBS) APPARATUS BASED ON HIGH REPETITION RATE PULSED LASER", filed on Sep. 4, 2015, by Sean Xiaolu Wang and Qun Li. The subject matter of the above mentioned U.S. application is hereby incorporated herein by reference in its entirety.

FIELD OF THE INVENTION

This invention generally relates to a laser induced breakdown spectroscopy (LIBS) apparatus, and more specifically to a laser induced breakdown spectroscopy (LIBS) apparatus based on high repetition rate pulsed laser.

BACKGROUND

Laser induced breakdown spectroscopy (LIBS) is a type of atomic emission spectroscopy which uses a highly energetic laser pulse as the excitation source. The laser pulse generates a high temperature micro-plasma on the surface of the sample. After this excitation, light that is characteristic of the elemental composition of the sample is emitted and analyzed within a spectrometer. LIBS has become a very popular analytical method in view of some of its unique features such as applicability to any type of sample, practically no sample preparation, remote sensing capability, and speed of analysis.

Traditional laser induced breakdown spectroscopy (LIBS) apparatus is based on single-shot lasers or lasers with very low repetition rate of <10 Hz. These lasers suffer from pulse to pulse variation in pulse energy, pulse width, peak power, etc., which induces instability in the intensity and duration of the produced micro-plasma emissions. This instability limits the capability of traditional LIBS apparatus for performing quantitative analysis of the subject sample. In addition, LIBS is a point measurement technique in which the size of the sample under analysis is typically limited to sub-millimeter (mm) per measurement point. However, samples under measurement generally have various level of non-uniformity. In order to get a consistent measurement result, multiple points on the sample surface need to be measured. Conventionally, this is achieved by mechanically moving the sample in reference to the laser beam or by scanning/deflecting the laser beam using one-dimensional (1-D) or two-dimensional (2-D) mirrors, such as galvanometer mirrors or MEMS mirrors. Sometimes this is combined with a servo focusing mechanism for automatically focusing the laser beam onto various depths on an uneven surface. For traditional LIBS systems, this process is very time-consuming since they can only measure a few measurement points per second due to the low repetition rate of the excitation laser.

SUMMARY OF THE INVENTION

It is thus the goal of the present invention to provide a laser induced breakdown spectroscopy (LIBS) apparatus based on a high repetition rate pulsed laser. The laser produces a train of laser pulses at a high repetition rate in the kHz or even higher range. When the laser beam hits the sample, it generates several thousands of micro-plasma emissions per second. Synchronized miniature CCD array optical spectrometer modules collect the LIBS signal from these micro-plasma emissions. By adjusting the integration time of the spectrometer to cover a plurality of periods of the laser pulse train, the spectrometer integrates the LIBS signal produced by this plurality of laser pulses. Hence the intensity of the obtained LIBS spectrum can be greatly improved to increase the signal-to-noise ratio (SNR) and lower the limit of detection (LOD). In addition, the influence of pulse to pulse variation of the laser is minimized since the obtained LIBS spectrum is the spectrum of a plurality of micro-plasma emissions produced by a plurality of laser pulses. The high repetition rate laser also makes it possible to measure the LIBS signal at a short and a long integration time and mathematically combining the two spectra to obtain a LIBS spectrum with enhanced dynamic range.

BRIEF DESCRIPTION OF THE FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1:
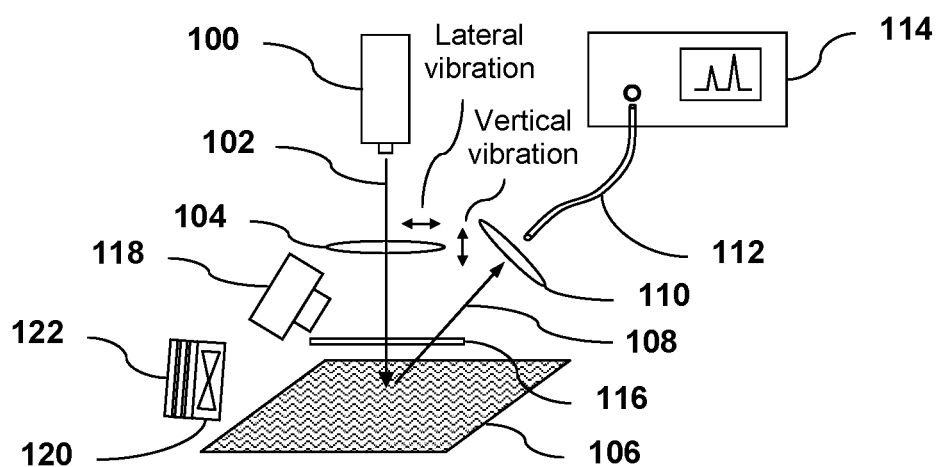
FIG. 1 illustrates an exemplary embodiment of the laser induced breakdown spectroscopy (LIBS) apparatus based on high repetition rate pulsed laser.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of method steps and apparatus components related to a laser induced breakdown spectroscopy (LIBS) apparatus based on high repetition rate pulsed laser. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

An exemplary embodiment of the laser induced breakdown spectroscopy (LIBS) apparatus is shown in FIG. 1. The LIBS apparatus comprises a pulsed laser 100 as the excitation light source. The pulsed laser 100 is a passively or actively Q-switched laser, or a mode-locked laser, or more preferably a passively Q-switched diode pumped solid state (DPSS) laser, which is capable of producing a train of laser pulses at a high repetition rate of >100 Hz, more preferably >1000 Hz (1 KHz). The pulse width of the laser is preferably less than 20 nanoseconds (ns), and more preferably less than 1 nanosecond (ns). The laser beam 102 from the pulsed laser 100 is focused by an objective lens 104 onto a surface of the sample 106. The laser pulse produces a plasma emission, i.e. LIBS signal 108 at the surface of the sample 106, which is collected by a focusing lens 110 to be focused into a light guide 112, such as an optical fiber or fiber bundle. The light guide 112 then delivers the LIBS signal 108 into an optical spectrometer device 114 for spectral analysis. The LIBS apparatus further comprises an optical window 116 in front of the objective lens 104 to protect its optical components from contamination. In a slight variation of the LIBS apparatus, the objective lens 104 and the focusing lens 110 may be replaced with other types of optical focusing elements, such as concave mirrors, to avoid chromatic aberration of the optical lenses. In yet another variation of the present embodiment, the objective lens 104 may be replaced with a Bessel beam generator, such as an axicon lens or an acoustic gradient lens which offers a larger focus depth than a conventional lens. The Bessel beam generator converts the laser beam 102 from Gaussian beam into Bessel beam, which is capable of maintaining a tight focus over a relatively long distance. This helps to overcome the reproducibility issue of LIBS signal caused by uneven sample surface. In addition, the Bessel beam is less susceptible to scattering caused by dust in the environment.

By adjusting the integration time of the spectrometer device 114 to cover a plurality of periods of the laser pulse train, the spectrometer device 114 can integrate the LIBS signal produced by a plurality of laser pulses. Hence the intensity of the obtained LIBS spectrum can be greatly improved to increase the signal-to-noise ratio (SNR) of the obtained LIBS spectrum. This unique feature of the high repetition rate laser based LIBS system allows it to measure trace elements with very low concentration, hence reducing the limit of detection (LOD) of the LIBS system. The increased signal intensity also lessens the sensitivity requirement for the optical spectrometer device 114. In addition, the energy of individual pulses in the laser pulse train can be reduced in comparison to conventional single shot or low repetition rate laser based LIBS system to obtain the same signal level. Hence the laser pulse is less invasive to the sample. Since the obtained LIBS spectrum is the spectrum of a plurality of micro-plasma emissions produced by a plurality of laser pulses, the influence of pulse to pulse variation of the laser is also minimized.

The high repetition rate laser enables fast scanning of the sample surface either to minimize the influence of sample non-uniformity or to perform spectral imaging of the sample. Referring back to FIG. 1, the objective lens 104 is mounted on a vibration motor (not shown) or other types of vibration device, which causes the objective lens 104 to vibrate in a direction perpendicular to the laser beam (parallel with the sample surface). The vibration pattern can be either 1-dimensional (1-D) or 2-dimensional (2-D), which results in 1-dimensional (1-D) or 2-dimensional (2-D) lateral movement of the laser beam over the sample surface. Thus the laser beam is scanned over an area of the sample surface to excite LIBS signal from multiple measurement points. The optical spectrometer device 114 operates in a continuous mode to collect the LIBS signal from all these measurement points and obtains the corresponding LIBS spectra. Additionally, the vibration motor may cause the objective lens 104 to vibrate in a direction parallel with the laser beam (perpendicular to the sample surface). This vibration causes the laser beam to be focused at different depths on the sample surface. Thus the laser beam can produce plasma emission from at least a portion of the measurement points even though the sample surface is uneven.

The vibration pattern of the objective lens 104 need not to be servo controlled in the present embodiment, which greatly simplifies the optical and mechanical design of the system. Further, the vibration pattern can be random or irregular in nature with a predefined maximum vibration range, causing the laser beam to move over an entire area on the sample surface. This laser beam movement, combined with the high repetition rate of the pulsed laser 100, allows one to collect LIBS spectra from hundreds or thousands of measurement points in just a few seconds. By performing an averaging of these spectra with a processor unit, the spectral variation caused by sample non-uniformity can be greatly reduced. The laser beam is further focused at different depths on the sample surface if a vertical lens vibration as disclosed above is incorporated. Thus the laser beam can produce strong plasma emission from at least a portion of the measurement points even though the sample surface is uneven. This allows one to obtain high quality LIBS spectra from at least a portion of the measurement points for an uneven surface. A predefined sorting or mathematical post-processing of the collected spectra may be performed with a processor unit to select the LIBS spectra from those in-focus measurement points, thus obtaining a more reproducible and accurate result. In comparison with the servo focusing mechanism used in conventional LIBS system, the above disclosed technique does not require any complicated feedback control, hence greatly simplifies the optical and mechanical design of the LIBS system. In addition, this variation in focus depth may be utilized for revealing additional material information related to the changing plasma emission due to laser power density variation as result of focus depth change. In a slight variation of the present embodiment, the vibration range (in both lateral and vertical directions) of the objective lens 104 and the energy level of the laser pulse can be feedback controlled in accordance to the quality (e.g. the signal-to-noise ratio) of the collected the LIBS spectra to obtain the optimum measurement result. For example, the vibration range of the objective lens 104 in the vertical direction can be feedback controlled in accordance to the number of collected LIBS spectra which are 'in-focus' to the surface of the sample. The vibration range of the objective lens 104 in the lateral direction can be feedback controlled in accordance to the variation of the collected LIBS spectra, which reflects the uniformity of the sample. The energy level of the laser pulse can be feedback controlled in accordance to the intensity or signal-to-noise ratio of the collected LIBS spectra.

Referring back to FIG. 1, the position of the laser beam on the sample surface may be monitored and recorded by a camera device 118. The position information is then correlated to the obtained LIBS spectrum of the corresponding measurement point to construct a two dimensional (2-D) spectral mapping of the sample surface.

As another feature of the present invention, the LIBS apparatus is equipped with an air curtain to prevent or reduce contaminant deposition onto its optical components. As disclosed above, the LIBS laser ablates a small amount of material from the sample. This material may deposit onto the optical components, such as the optical window 116 and the objective lens 104, of the LIBS apparatus. Continued accumulation of these materials will contaminate the optical components and reduce both the intensity of the laser pulse and the intensity of the collected LIBS signal. This problem is solved by introducing an air curtain between the optical window 116 and the surface of the sample 106. Referring to FIG. 1, the air curtain is produced by a forced air flow generator, e.g. a fan 120 with a pre-filtering system 122. External air passing through the pre-filtering system 122 is filtered and then accelerated by the fan 120 to generate a forced air flow between the sample 106 and the exit optics, i.e. the objective lens 104 and the optical window 116 of the LIBS apparatus. The forced air flow acts as an air curtain for preventing or reducing the laser-ablated material from deposition onto the exit optics of the LIBS apparatus. It can also be used as an air gun for pre-cleaning the sample surface or for cooling down the temperature of the measurement area. Further, the pre-filtering system 122 may filter and extract nitrogen gas from the atmosphere. The nitrogen gas is supplied to the sample surface as purge gas for increasing the LIBS signal intensity in the ultraviolet (UV) wavelength region and enhancing the LIBS signal for certain elements, e.g. carbon and sulfur, which have strong spectral lines in the UV region. In a slight variation of the present embodiment, the pre-filtering system 122 may be combined with an inert gas generation system or a compressed gas system to supply inert gas (e.g. argon, helium) to the sample surface. The inert gas will help increase the intensity of the spectral lines in the deep UV region, which may be re-absorbed by the air if the LIBS measurement is performed under open air condition.

Figure 2A:
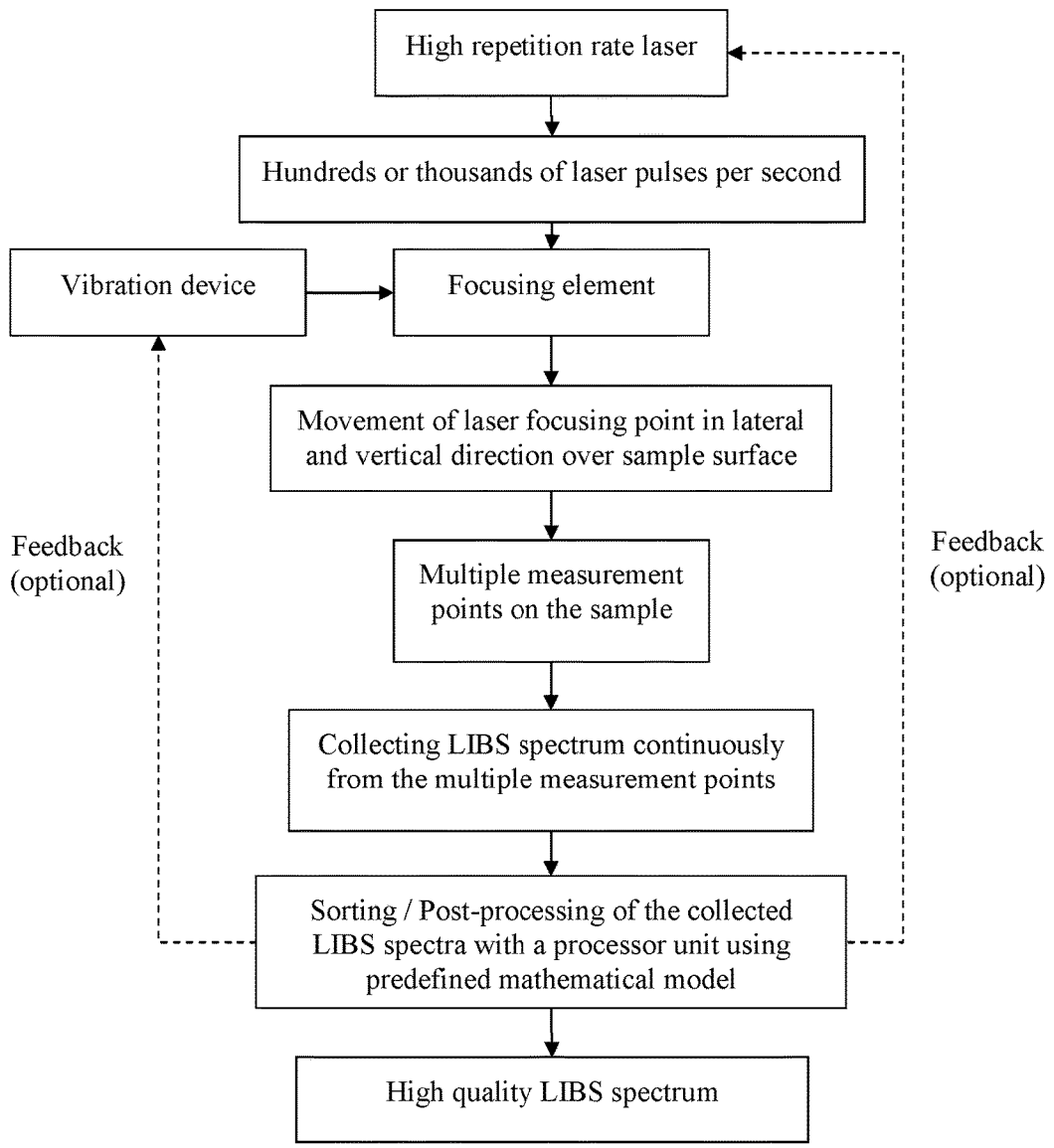
FIG. 2a is a flowchart for the high repetition rate laser based LIBS system.
Figure 2B:
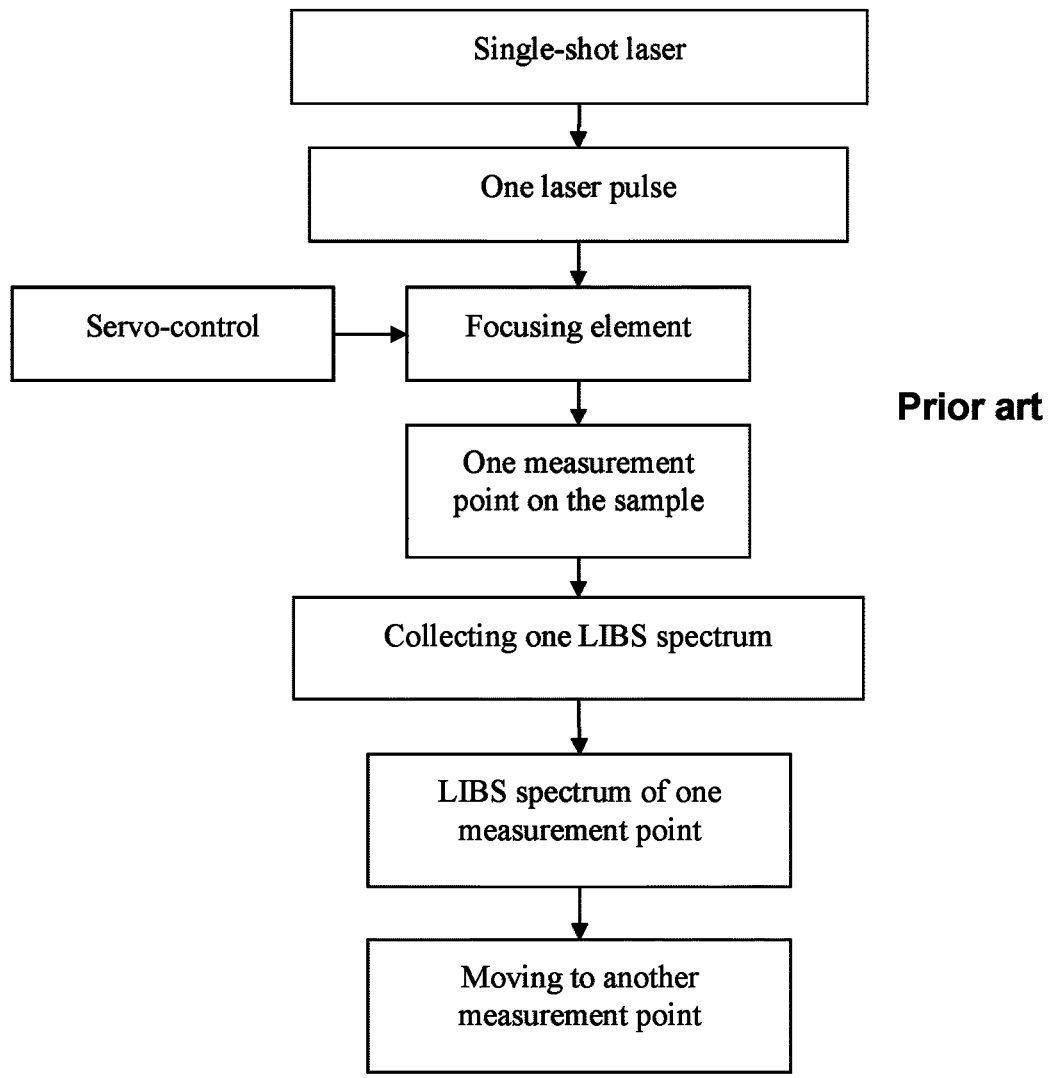
FIG. 2b is a flowchart for the conventional single-shot or low repetition rate laser based LIBS system for comparison.

A comparison of the presently disclosed high repetition rate laser based LIBS system and conventional single-shot laser based LIBS system is shown in FIG. 2. In conventional single-shot laser based LIBS system as shown in FIG. 2b, the LIBS laser produces one laser pulse at a time. The laser beam is focused onto the sample by providing servo-control to the focusing element. The laser beam then excites plasma emission from one measurement point on the sample. The optical spectrum of the plasma emission is measured to obtain the LIBS spectrum of the measurement point. The laser beam is then moved to another measurement point to measure the LIBS spectrum thereof. In the high repetition rate laser based LIBS system as shown in FIG. 2a, the LIBS laser operates continuously, producing hundreds or thousands of laser pulses per second. The laser beam is focused by a focusing element, which is vibrated by a vibration device to scan the laser beam over an area of the sample to excite LIBS signal from multiple measurement points. In addition, the focusing element may be vibrated in a direction perpendicular to the sample surface. This vibration causes the laser beam to be focused at different depths on the sample surface, thus producing plasma emission from at least a portion of the measurement points even though the sample surface is uneven. The spectrometer device collects LIBS spectrum continuously from the plurality of measurement points. A predefined sorting or other kinds of mathematical post-processing of the collected spectra is performed with a processor unit to select the LIBS spectra with the best quality (e.g. best signal-to-noise ratio). As an option, the quality (e.g. signal-to-noise ratio) of the collected LIBS spectra may be utilized to provide feedback control to the vibration device and the high repetition rate laser in order to obtain the optimum measurement result. The high repetition rate laser based LIBS system is capable of measuring the LIBS spectra of multiple measurement points in a very short period of time. This help to solve the sample non-uniformity issue. In addition, by integrating the LIBS signal produced by a plurality of laser pulses, the intensity of the obtained LIBS spectrum can be greatly improved, making it possible to measure trace elements with very low concentration. Further, the energy level of individual laser pulses in the laser pulse train can be reduced to make the laser pulse less invasive to the sample.

Figure 3:
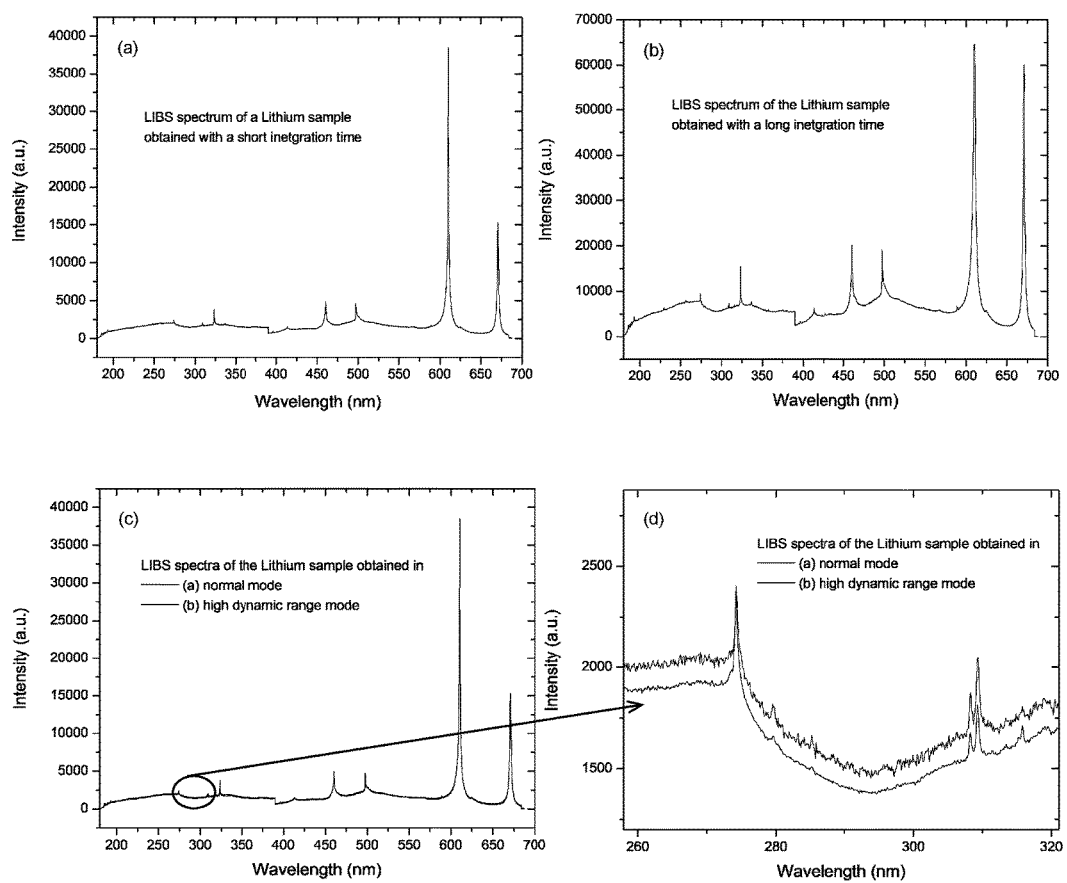
FIG. 3 shows an example of combining a LIBS spectrum obtained with a short integration time and a LIBS spectrum obtained with a long integration time to produce a LIBS spectrum with enhanced dynamic range.

Utilizing the high repetition rate of the pulsed laser 100, it is possible to further enhance the dynamic range of the obtained LIBS spectrum, which is defined as the ratio of the maximum detectable signal level to the minimum detectable signal level. One example of the approach is shown in FIG. 3, where a handheld LIBS apparatus is employed to measure a Lithium sample with trace level of Aluminum and Magnesium impurities. The handheld LIBS apparatus comprises a high repetition rate pulsed laser as disclosed above as well as a miniature CCD array spectrometer. FIG. 3a shows the LIBS spectrum of the Lithium sample measured at a relatively short integration time. The spectrum has a limited dynamic range of <1,000 due to the relatively shallow well depth and high readout and dark noise of the CCD array in the miniature spectrometer. FIG. 3b shows the LIBS spectrum of the same Lithium sample measured at a relatively long integration time. Since more plasma emissions are collected by the CCD array spectrometer during the longer integration time, the weak plasma emission bands of the trace elements become more observable. Yet the strong plasma emission bands of the matrix element (Lithium in this case) become saturated. By mathematically combining the two spectra, it is possible to obtain a LIB S spectrum with enhanced dynamic range.

One exemplary approach of combining the two spectra consists of three steps. In the first step, both the long integration time spectrum and the short integration time spectrum are divided into two spectral regions: a saturated spectral region where the signal level of the long integration time spectrum is above a pre-defined threshold and an unsaturated spectral region where the signal level of the long integration time spectrum is below the threshold. In the second step, an intensity ratio is calculated between the long integration time spectrum and the short integration time spectrum for the unsaturated spectral region. The long integration time spectrum is then divided by this ratio to obtain a normalized long integration time spectrum. In the third step, a combined spectrum is produced by combining the short integration time spectrum at the saturated spectral region with the normalized long integration time spectrum at the unsaturated spectral region. To reduce the influence of the spectral baseline, the derivative of the two spectra may be used to calculate their intensity ratio.

FIGS. 3c and 3d show a comparison of the LIBS spectra of the Lithium sample obtained in a normal mode and a high dynamic range mode of the handheld LIBS apparatus, where FIG. 3d is a zoomed view of FIG. 3c. In the normal mode, the LIBS spectrum is measured at a short integration time. In the high dynamic range mode, the LIBS spectrum is measured at a short and a long integration time. The two spectra are then combined with the above disclosed approach to obtain a combined spectrum. It can be seen that the noise level of the spectrum is greatly reduced in the high dynamic range mode, yielding a dynamic range of >10,000, which is one order of magnitude enhancement. The dynamic range can be further enhanced by using an even longer integration time, making the sensitivity of the handheld LIBS apparatus rival that of benchtop LIBS systems and allowing for the measurement of elements at trace (ppm or sub ppm) levels. The above disclosed approach facilitates the development of portable or handheld LIBS apparatus, which is a key step of introducing LIBS technology into field applications.

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. A laser induced breakdown spectroscopy (LIBS) apparatus for measuring the LIBS spectrum of a subject, the LIBS apparatus comprising:
   a high repetition rate pulsed laser light source configured to produce a laser beam in the form of a plurality of laser pluses at a high repetition rate;
   an optical focusing element configured to focus the laser beam onto a surface of the subject, wherein the plurality of laser pluses produce a plurality of plasma emissions from the surface of the subject;
   an optical spectrometer device configured to measure an optical spectrum of the plurality of plasma emissions at a short integration time and a long integration time to obtain at least two LIBS spectra and mathematically combine the at least two LIBS spectra to obtain a LIBS spectrum with enhanced dynamic range.

2. The laser induced breakdown spectroscopy (LIBS) apparatus of claim 1, wherein the repetition rate of the laser pulse is greater than 100 Hz.

3. The laser induced breakdown spectroscopy (LIBS) apparatus of claim 1, wherein the repetition rate of the laser pulse is greater than 1000 Hz.

4. The laser induced breakdown spectroscopy (LIBS) apparatus of claim 1, wherein the laser pulses have a pulse width of less than 20 nanoseconds (ns).

5. The laser induced breakdown spectroscopy (LIBS) apparatus of claim 1, wherein the laser pulses have a pulse width of less than 1 nanosecond (ns).

6. The laser induced breakdown spectroscopy (LIBS) apparatus of claim 1, wherein the optical focusing element comprises an optical lens.

7. The laser induced breakdown spectroscopy (LIBS) apparatus of claim 1, wherein the optical focusing element comprises an optical mirror.

8. The laser induced breakdown spectroscopy (LIBS) apparatus of claim 1, further comprising a vibration device configured to vibrate the optical focusing element to scan the laser beam over an area on the surface of the subject, wherein the laser beam produces a plurality of plasma emissions from a plurality of measurement points on the surface of the subject.

9. The laser induced breakdown spectroscopy (LIBS) apparatus of claim 8, wherein the vibration device vibrates the optical focusing element in a direction parallel with the surface of the subject.

10. The laser induced breakdown spectroscopy (LIBS) apparatus of claim 8, wherein the vibration device vibrates the optical focusing element in a direction perpendicular to the surface of the subject.

11. The laser induced breakdown spectroscopy (LIBS) apparatus of claim 8, wherein the vibration device produces a 1-dimensional (1-D) vibration pattern.

12. The laser induced breakdown spectroscopy (LIBS) apparatus of claim 8, wherein the vibration device produces a 2-dimensional (2-D) vibration pattern.

13. The laser induced breakdown spectroscopy (LIBS) apparatus of claim 8, wherein the vibration device produces a 3-dimensional (3-D) vibration pattern.

14. The laser induced breakdown spectroscopy (LIBS) apparatus of claim 8, wherein the vibration device produces a random vibration pattern.

15. The laser induced breakdown spectroscopy (LIBS) apparatus of claim 1, further comprising a camera device configured to monitor and record a position of the laser beam on the surface of the subject.

16. The laser induced breakdown spectroscopy (LIBS) apparatus of claim 1, wherein the optical focusing element comprises a Bessel beam generator.

* * * * *